United States Patent [19]

Kamen et al.

[11] Patent Number: 4,978,524
[45] Date of Patent: Dec. 18, 1990

[54] GLOSSY COSMETIC PRODUCT AND METHOD OF PRODUCING SAME

[75] Inventors: Melvin E. Kamen, Highlands; Philip Bernstein, Glen Ridge; Augustine Defazio, Englishtown, all of N.J.

[73] Assignee: Revlon, Inc., New York, N.Y.

[21] Appl. No.: 296,230

[22] Filed: Jan. 12, 1989

[51] Int. Cl.$^5$ .................... A61K 7/021; A61K 7/025; A61K 7/027; A61K 7/031
[52] U.S. Cl. .......................... 424/64; 424/78; 424/DIG. 5; 427/40; 427/41; 427/43.1
[58] Field of Search .................... 424/64, 78, DIG. 5; 427/40, 41, 43.1

[56] References Cited

U.S. PATENT DOCUMENTS

| | | | |
|---|---|---|---|
| 3,403,040 | 9/1968 | Osipow | 424/64 |
| 4,072,769 | 2/1978 | Lidel | 427/38 |
| 4,188,426 | 2/1980 | Auerbach | 427/40 |
| 4,264,750 | 4/1981 | Anand et al. | |
| 4,296,151 | 10/1981 | Boultinghouse | |
| 4,404,256 | 9/1983 | Anand et al. | |
| 4,467,075 | 8/1984 | Taracon | |
| 4,491,653 | 1/1985 | McGinniss et al. | |
| 4,508,781 | 4/1985 | Yagi et al. | |
| 4,557,945 | 12/1985 | Yagi et al. | 427/40 |
| 4,593,050 | 6/1986 | Cohen et al. | |
| 4,801,495 | 1/1989 | Fukui et al. | 424/69 |
| 4,844,986 | 7/1989 | Karakelle et al. | 427/41 |

FOREIGN PATENT DOCUMENTS 55-99932 7/1980 Japan .
765,545 1/1957 United Kingdom .

OTHER PUBLICATIONS

Anand et al, Surface Modification of Low Density Polyethylene in a Fluorine Gas Plasma Polymer, 1981, vol. 22, (pp. 361-371 thru appendix III).
Anand et al., Surface Characterization of Plasma--Fluorinated Polymers ACS Symposium Series No. 162, 1981, (pp. 333-370).
Corbin et al., Kinetics of Polymer Surface Fluorination: Elemental and Plasma-Enhanced Reactions, Polymer Reports, 1982, (pp. 1-3).
Corbin et al., Surface Fluorination of Polymers in a Glow Discharge Plasma Photochemistry, American Chemical Society, 1985, (pp. 98-103).

*Primary Examiner*—Merrell C. Cashion, Jr.
*Assistant Examiner*—Amy Hulina

[57] ABSTRACT

A cosmetic product, such as lipstick, is provided with a surface layer having a wetting angle less than the normal wetting angle of the cosmetic product. The surface layer, which can be formed by subjecting the cosmetic product to a plasma treatment process, allows a material having an ultra-glossy finish and having poor adhesion with objects which have a wetting angle in the neighborhood of the normal wetting angle of the cosmetic product to be adhered to the surface layer and hence to the cosmetic product.

14 Claims, 3 Drawing Sheets

GLOSSY COSMETIC PRODUCT AND METHOD OF PRODUCING SAME

FIELD OF THE INVENTION

The present invention relates to lipstick and other cosmetic products having an ultra-glossy finish, and, in addition, to a method for providing such products with a finish which is so glossy that a "wet look" is achieved.

BACKGROUND OF THE INVENTION

In the manufacture of lipstick, a molding process is conventionally used. As a result of the adhesion between the lipstick and the mold, problems are often encountered in releasing the lipstick from the mold. The poor release of the lipstick from the mold often causes the lipstick to have a non-uniform matte finish (i.e., a finish which is flat or dull and characterized by numerous surface irregularities). Because such a non-uniform matte finish gives lipstick a noncosmetic appearance, efforts have been made to provide lipstick with a shinier and more uniform (i.e., a more cosmetic) appearance.

One common technique for eliminating the nonuniform matte finish on molded lipstick involves "flaming" the lipstick after it has been removed from the mold. While flaming has been found to improve the finish of the lipstick, the degree of improvement is limited. Thus, ultra-glossy or "wet look" finishes cannot be achieved by flaming. Moreover, some lipsticks, such as those with molded indicia or those with low melting temperatures, are not suitable for flaming. Thus, there is a real need for an alternate post-molding treatment technique for lipstick which improves the finish of the molded lipstick.

SUMMARY OF THE INVENTION

The present invention involves decreasing the wetting angle of a cosmetic product, such as lipstick, to thereby permit the adhesion of a material which, in its liquid state, would not otherwise adhere to the cosmetic product. The wetting angle (or contact angle) is the measurement of the angle which exists between a liquid and a solid surface. This measurement gives an indication of the relative values of the forces of adhesion and cohesion that result in interfacial tension. As used herein, the term "wetting angle" describes the ability of a specified solid surface (i.e., the cosmetic product) to be wet by a specified liquid under defined conditions. Thus, the smaller the wetting angle of the cosmetic product, the greater is the "wettability" of its surface by the specified liquid.

In one embodiment, the wetting angle of the cosmetic product is decreased by modifying the surface composition of the cosmetic product so as to obtain a surface layer having a wetting angle which is less than the normal wetting angle of the cosmetic product. A material having an ultra-glossy finish and having poor adhesion with objects which have a wetting angle in the neighborhood of the normal wetting angle of the cosmetic product can then be adhered to the surface layer in the form of an outer layer. If the cosmetic product is lipstick, one especially advantageous technique for decreasing its wetting angle involves subjecting the lipstick to a plasma treatment process which converts the normal hydrocarbon surface of the lipstick to a more easily wettable surface layer having a wetting angle sufficient to permit the adhesion of an outer layer of, for example, silicone or any other suitable silicon derivative.

BRIEF DESCRIPTION OF THE DRAWINGS

For a better understanding of the invention, reference is made to the following detailed description considered in conjunction with the accompanying drawings, in which.

DETAILED DESCRIPTION

Although the present invention has applicability to many different cosmetic products, it is especially suitable for use in connection with lipstick. Accordingly, the present invention will be described below in connection with lipstick.

Figure 1:
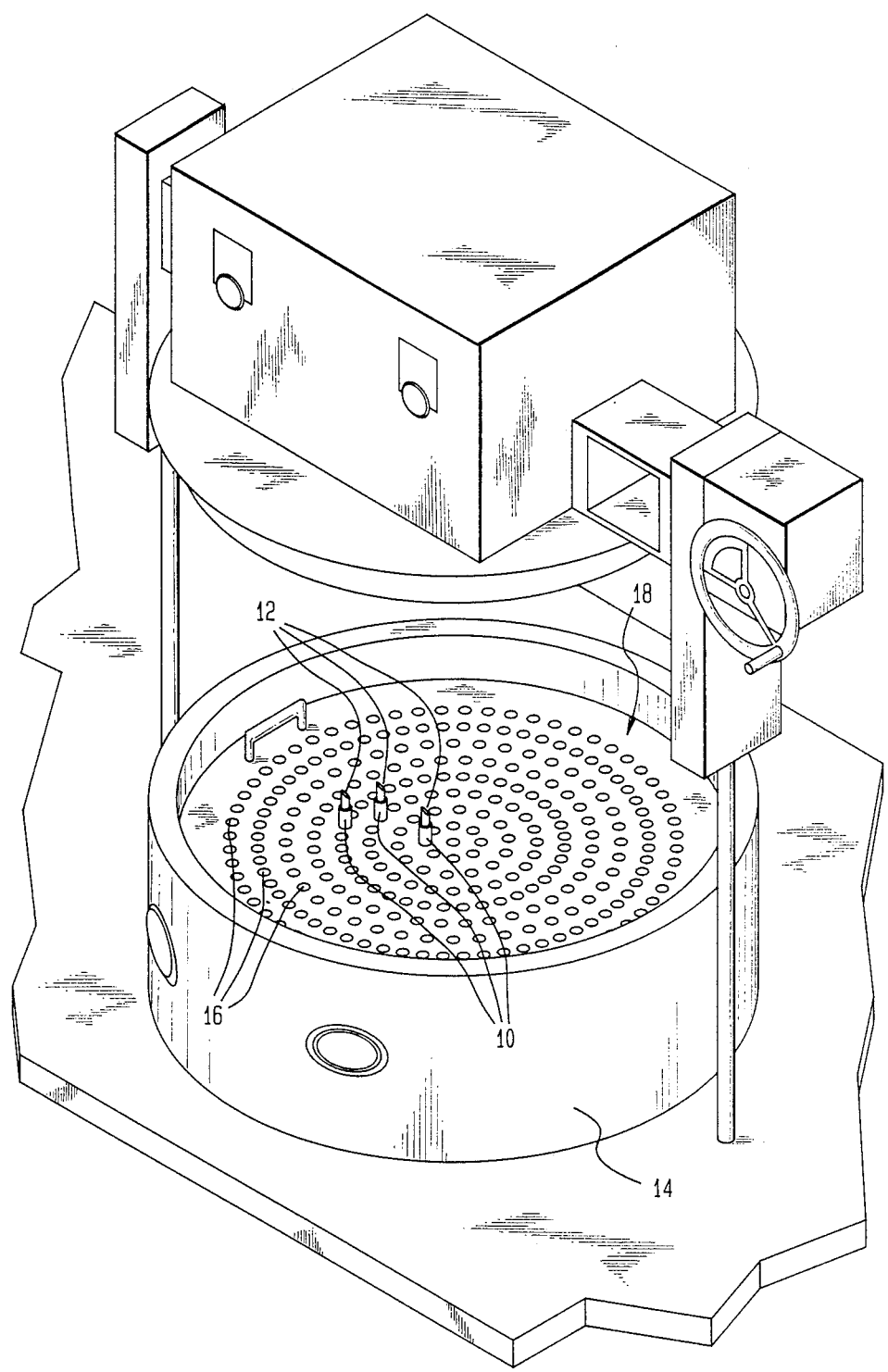
FIG. 1 is a detailed perspective view of a vacuum chamber which is used in connection with a chemical vapor deposition system illustrated diagrammatically in FIG. 3, the vacuum chamber being shown in its open position in order to facilitate consideration and discussion.
Figure 2:
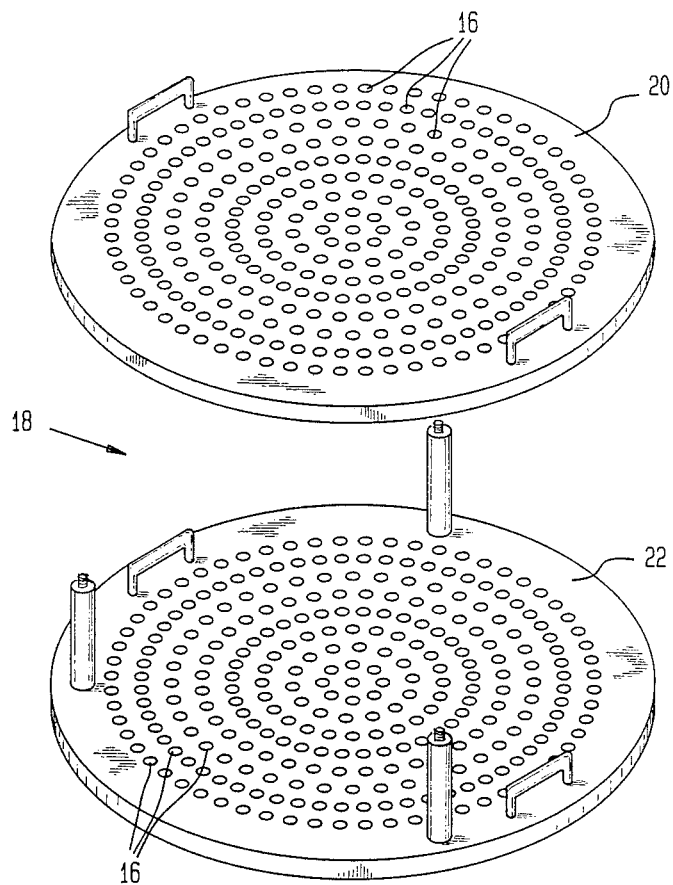
FIG. 2 is an exploded perspective view of a fixture which is used in the vacuum chamber illustrated in FIG. 1.

With reference to FIG. 1, sticks 10 of lipstick 12 are mounted in an upright position in a vacuum chamber 14. The sticks 10 are received in openings 16 provided in a fixture 18, which is removably mounted in the vacuum chamber 14. When the vacuum chamber 14 is operating at full capacity, all of the openings 16 in the fixture 18 would receive a stick 10 of lipstick 12. In order to maximize the capacity of the vacuum chamber 14, the fixture 18 has a tiered construction (see FIG. 2), whereby the fixture 18 includes an upper tier 20 and a lower tier 22. Once the vacuum chamber 14 has been loaded, it is closed in preparation for the performance of a plasma treatment process using a chemical vapor deposition system 24 (see FIG. 3).

Figure 3:
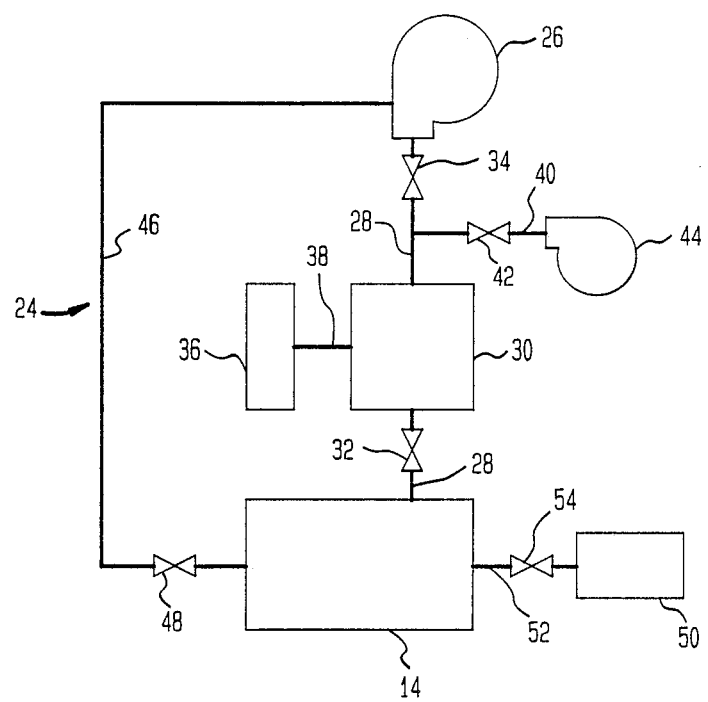
FIG. 3 is a flow diagram of a system which incorporates the vacuum chamber illustrated in FIG. 1 and which performs a plasma treatment process in accordance with one step of a new and improved method for providing lipstick with an ultra-glossy finish.

Referring now to FIG. 3, a chemical vapor deposition system 24 includes, in addition to the vacuum chamber 14, a vacuum pump 26, which is connected to the vacuum chamber 14 by a foreline 28. A cold trap 30 is positioned in the foreline 28 between the vacuum chamber 14 and the vacuum pump 26. The foreline 28 includes a valve 32 between the vacuum chamber 14 and the cold trap 30. Another valve 34 is positioned in the foreline 28 between the vacuum pump 26 and the cold trap 30. A refrigerant unit 36 supplies refrigerant to the cold trap 30 through a line 38. A line 40, which is provided with a valve 42, connects a holding pump 44 to the foreline 28 between the valve 34 and the cold trap 30. The vacuum pump 26 is also connected to the vacuum chamber 14 by a roughing line 46, which includes a valve 48. Treatment gas is supplied from a source 50 to the vacuum chamber 14 through a line 52, which includes a valve 54.

With the valves 42 and 48 open and the valves 32, 34 and 54 closed, the vacuum chamber 14 is evacuated through the roughing line 46 by the vacuum pump 26 until a vacuum measurement of 50 microns or less is achieved. After such a vacuum has been created in the vacuum chamber 14, the valves 42 and 48 are closed and the valves 32 and 34 are opened. When a vacuum measurement of 5 microns or less is reached, the valve 54 is opened to permit treatment gas, such as $C_2F_4$, $SiF_4$, $F_2$, $CF_4$ or the like, to bleed into the vacuum chamber 14 until a vacuum measurement of about 50 microns is reached.

Figure 4:
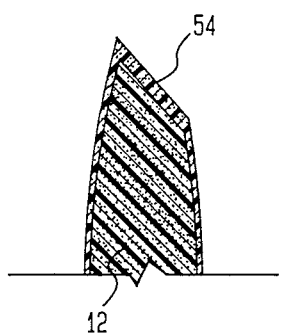
FIG. 4 is a cross-sectional view of lipstick which has undergone treatment by the system illustrated in FIG. 3.
Figure 5:
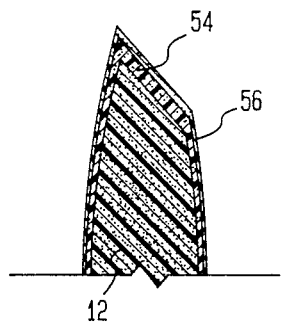
FIG. 5 is a cross-sectional view of the lipstick illustrated in FIG. 4 after undergoing a further treatment step.

The treatment gas is maintained in the vacuum chamber 14 for a length of time, usually about 2 to 15 minutes, sufficient to permit the treatment gas to saturate the surface of the lipstick 12 contained in the vacuum chamber 14. At the end of the saturation period, the cathode (not shown) of the vacuum chamber 14 is energized to generate a plasma throughout the vacuum chamber 14. The plasma, in turn, causes a chemical reaction between the treatment gas and the lipstick 12. As a result of such a chemical reaction, the surface composition of the lipstick 12 is modified so as to obtain a surface layer 54 (see FIG. 4) having a wetting angle which is less than the normal wetting angle of the lipstick, as well as cladding-like characteristics which will be discussed hereinafter. Typically, the surface layer 54 has a thickness in a range of from about 10 angstroms to about 300 angstroms.

If the treatment gas is $C_2F_4$, $C_2F_6$, $SiF_4$, $F_2$, $CF_4$ or the like, the surface layer 54 would be more wettable to non-polar compounds, such as fluorinated oils, etc. By using air as the treatment gas, the surface layer 54 would be more wettable to polar compounds, such as water, alcohol, etc.

At the conclusion of the plasma treatment process (usually about 2 to 15 minutes), the valves 32 and 34 are closed, while the valve 54 is left open until the vacuum chamber 14 is up to air (i.e., is at atmospheric pressure). Now, the valve 54 can be closed and the vacuum chamber 14 can be opened. After opening the vacuum chamber 14, the sticks 10, with their plasma-treated lipstick 12, are removed from the fixtures 18. Because the plasma treatment is conducted at room temperature, the lipstick 12 does not undergo any appreciable distortion.

Due to the fact that some lipstick contains moisture, the cold trap 30, which is maintained under vacuum at all times by either the vacuum pump 26 or the holding pump 44, must be employed to collect any moisture removed from the lipstick 12 during the evacuation of the vacuum chamber 14 and thereby prevent such moisture from contaminating the vacuum pump 26. Actually, moisture is removed from the boundary of the lipstick 12 only, leaving the interior of the lipstick 12 with basically the same moisture content that it had prior to the performance of the plasma treatment process described above.

The treatment gas could be any gas which contains fluorine or another halogen. In fact, any plasma reactive gas capable of bonding (chemically and possibly mechanically) to the surface of the lipstick 12 could be used as the treatment gas. Even non-plasma reactive gasses might be employed as the treatment gas.

The next processing step involves the application of an outer layer 56 (see FIG. 6) of silicone or any other suitable silicon derivative to the plasma-treated lipstick 12. Because silicone and most, if not all, of the other suitable silicon derivatives are soluble in castor oil and because most lipstick formulations include castor oil, the surface layer 54 is necessary to function as a cladding-like barrier between the rest of the lipstick 12 and the outer layer 56 so that the outer layer 56 will adhere to the lipstick 12. Also, the waxes, castor oil and wetting agents commonly found in lipstick formulations tend to repel silicone and most, if not all, of the other suitable silicon derivatives. By plasma treating the lipstick 12, its wetting angle is decreased as a result of the formation of the surface layer 54, thereby providing the required adhesion between the lipstick 12 and the outer layer 56.

One method of forming the outer layer 56 involves dipping the plasma-treated lipstick 12 into a mixture which is about 10% to 20% solids by weight silicone oil or fluorinated silicone and about 80% to 90% by weight Freon or some other suitable solvent which promotes the drying of the fluorinated silicone and controls the thickness of the outer layer 56. The resulting outer layer 56, which covers the entire exterior surface of the plasma-treated lipstick 12, has a thickness in a range of from about 0.1 microns to about 0.2 microns. An alternate method of forming the outer layer 56 involves applying a drop of silicone directly to the tip of the plasma-treated lipstick 12 and then allowing the silicone to migrate over the entire exterior surface thereof. It would also be possible to spray the silicone directly onto the plasma-treated lipstick 12.

Regardless of which method is employed to form the outer layer 56, the result is basically the same: the lipstick 12 has an ultra-glossy finish which gives the lipstick 12 a "wet look". Such a "wet look" offers an aesthetic advantage, especially for point of sale purposes. After at least its initial application, it is possible that the silicone-coated lipstick 12 could provide the user with a "wet look" and/or could inhibit chapping of the user's lips. It is also possible that the silicone from the outer layer 56 could migrate into the inner layer 54 after its initial use, whereby the foregoing advantages might be realized during subsequent uses of the lipstick 12.

It will be understood that the embodiments described herein are merely exemplary and that a person skilled in the art may make many variations and modifications without departing from the spirit and scope of the invention. For instance, the lipstick or other cosmetic product could be masked prior to its being plasma treated so that only selected portions will have an ultra-glossy or "wet look" finish, whereby the present invention could be used for decorating purposes. All such variations and modifications are intended to be included within the scope of the invention as defined in the appended claims.

We claim:

1. A wax-based cosmetic product made from a composition having a first wetting angle, comprising a first layer formed on the surface of said cosmetic product, said first layer being comprised of fluorine and having a second wetting angle which is less than said first wetting angle and a second layer adhered to said first layer, said second layer being made from a material having an ultra-glossy finish and having poor adhesion with objects having a wetting angle in the neighborhood of said first wetting angle.

2. A cosmetic product according to claim 1, wherein said first layer is produced by a plasma treatment process.

3. A cosmetic product according to claim 2, wherein said plasma treatment process is carried out using a gas selected from a group consisting of $C_2F_4$, $C_2F_6$, $SiF_4$, $F_2$ and $CF_4$.

4. A cosmetic product according to claim 2, wherein said first layer creates a barrier between said cosmetic product and said second layer.

5. A cosmetic product according to claim 4, wherein said cosmetic product is lipstick.

6. A cosmetic product according to claim 1, wherein said first layer is formed on a preselected portion of said cosmetic product, whereby only said preselected portion has an ultra-glossy finish.

7. A method of providing a waxed-based cosmetic product with an ultra-glossy finish, comprising the step of decreasing the wetting angle of said cosmetic product by forming a first layer comprising fluorine on the surface of said cosmetic product, said first layer having a second wetting angle which is less than said first wetting angle to thereby permit the adhesion of a second layer, said second layer being made from silicone or a fluorinated silicon having an ultra-glossy finish and having poor adhesion with objects having a wetting angle in the neighborhood of said first wetting angle.

8. A method according to claim 7, wherein said first layer is produced by a plasma treatment process.

9. A method according to claim 8, wherein said plasma treatment process is carried out using a gas selected from a group consisting of $C_2F_4$, $C_2F_6$, $SiF_4$, $F_2$ and $CF_4$.

10. A method according to claim 9, wherein said first layer creates a barrier between said cosmetic product and said second layer.

11. A method according to claim 10, wherein said cosmetic product is lipstick.

12. A method according to claim 7, wherein said first layer is formed on a preselected portion of said cosmetic product, whereby only said preselected portion has an ultra-glossy finish.

13. In a cosmetic product made from a waxed-based composition having a first wetting angle, the improvement wherein said first wetting angle is decreased by forming a first layer on the surface of said cosmetic product, said first layer being produced by a plasma treatment process which is carried out using a gas selected from a group consisting of $C_2F_4$, $C_2F_6$, $SiF_4$, $F_2$ and $CF_4$ and said first layer having a second wetting angle which is less than said first wetting angle to thereby permit the adhesion of a second layer made from silicone or fluorinated silicone having an ultra-glossy finish and having poor adhesion with objects having a wetting angle in the neighborhood of said first wetting angle.

14. A method of providing a wax-based cosmetic product with an ultra-glossy finish, comprising the step of decreasing the wetting angle of said cosmetic product by forming a first layer on the surface of said cosmetic product, said first layer being produced by a plasma treatment process which is carried out using a gas selected from a group consisting of $C_2F_4$, $C_2F_6$, $SiF_4$, $F_2$ and $CF_4$ and said first layer having a second wetting angle which is less than said first wetting angle to thereby permit the adhesion of a second layer made from silicone or a fluorinated silicone having an ultra-glossy finish and having poor adhesion with objects having a wetting angle in the neighborhood of said first wetting angle.

* * * * *